United States Patent
Ito

(10) Patent No.: US 11,243,137 B2
(45) Date of Patent: Feb. 8, 2022

(54) CYLINDER MANAGEMENT SYSTEM, CYLINDER MANAGEMENT PROGRAM AND GAS LEAK DETECTION SYSTEM

(71) Applicant: HORIBA, LTD., Kyoto (JP)

(72) Inventor: Kazuya Ito, Kyoto (JP)

(73) Assignee: HORIBA, LTD., Kyoto (JP)

( * ) Notice: Subject to any disclaimer, the term of this patent is extended or adjusted under 35 U.S.C. 154(b) by 299 days.

(21) Appl. No.: 16/412,816

(22) Filed: May 15, 2019

(65) Prior Publication Data

US 2019/0353551 A1 Nov. 21, 2019

(30) Foreign Application Priority Data

May 15, 2018 (JP) .............................. JP2018-093475

(51) Int. Cl.
*G01M 3/32* (2006.01)
*G06Q 10/08* (2012.01)

(52) U.S. Cl.
CPC ........ *G01M 3/3254* (2013.01); *G06Q 10/087* (2013.01)

(58) Field of Classification Search
CPC .. G01M 3/3254; G01M 15/02; G01M 15/102; G01M 3/3272; G01M 17/007; G01M 15/00; G06Q 10/087; G01N 33/0008; G01F 22/02
See application file for complete search history.

(56) References Cited

U.S. PATENT DOCUMENTS

2019/0121350 A1* 4/2019 Celia ...................... H04L 67/12

FOREIGN PATENT DOCUMENTS

| JP | 11-051827 A | 2/1999 |
| JP | 2002071525 A | 3/2002 |
| JP | 3796015 | 7/2006 |
| JP | 5718277 B2 | 5/2015 |
| JP | 2016-134596 A | 7/2016 |

OTHER PUBLICATIONS

The Partial EESR dated Oct. 9, 2919 issued for European Patent Application No. 19 174 166.9, 11 pgs.
Office Action dated Aug. 3, 2021 issued in JP patent application No. 2018-093475, 9 pgs.

* cited by examiner

*Primary Examiner* — Robert G Bachner
(74) *Attorney, Agent, or Firm* — Brooks Kushman P.C.

(57) ABSTRACT

This invention is to collectively manage the timing to replace the multiple gas cylinders, and is a cylinder management system that manages multiple gas cylinders that supply a utility gas of a calibration gas to multiple gas analysis device and that comprises multiple pressure sensors that that detect a pressure of each of the multiple gas cylinders, and a management device that calculates a cylinder gas residual quantity in each gas cylinder based on the pressure detected by each pressure sensor and manages the timing to replace each gas cylinder.

7 Claims, 5 Drawing Sheets

CYLINDER MANAGEMENT SYSTEM, CYLINDER MANAGEMENT PROGRAM AND GAS LEAK DETECTION SYSTEM

CROSS-REFERENCE TO RELATED APPLICATION

This application claims priority to Japanese Application No. 2018-093475, filed May 15, 2018, the disclosure of which is incorporated in its entirety by reference herein.

FIELD OF THE ART

This invention relates to a cylinder management system, a cylinder management program and a gas leak detection system.

BACKGROUND ART

In the background of fuel-efficient competition or coping with a regulation, complicated business or increase of workload such as motorization or connectivity, it is required experiments and tests be conducted efficiently in developing an automobile. In case of dealing with analyzers for experiments or test, it is necessary to verify the cylinder gas residual quantity of a gas cylinder into which a calibration gas is enclosed in advance or to update the concentration value of the calibration gas at a time of replacing the gas cylinder not to interrupt the experiments or the tests. In case of updating the concentration value of the calibration gas, most users take a note of the concentration value of the gas cylinder at hand and manually input and set the concentration value of the calibration gas in front of the analyzer.

A cylinder management system that makes it easy to set the concentration of the calibration gas is disclosed in the patent document 1. The test system shown in the patent document 1 is so configured that the kind of the span gas and the concentration of the span gas can be collected set for multiple analysis devices.

However, in order to verify the residual quantity of the cylinder gas in the multiple gas cylinders, it is necessary to go to the cylinder chamber where the gas cylinders are housed, and it takes time to go to the cylinder chamber placed various places and to verify the residual quantity of each cylinder gas. As a result of this, the period while the experiment and the test are interrupted becomes long. In addition, human errors might easily be caused due to verification error.

PRIOR ART DOCUMENTS

Patent Document

Patent document 1: Japanese Patent No. 5718277

SUMMARY OF THE INVENTION

Problems to be Solved by the Invention

This invention is to solve all of the problems and a main object of this invention is to collectively manage a timing to replace multiple cylinders.

Means to Solve the Problems

More specifically, a cylinder management system in accordance with this invention is a cylinder management system that manages multiple gas cylinders that supply a cylinder gas to a gas analysis device that analyzes an exhaust gas of a specimen as being a vehicle or a part of the vehicle, and is characterized by comprising multiple pressure sensors each of which detects a pressure of each of the multiple gas cylinders, and a management device that calculates a cylinder gas residual quantity in each of the gas cylinders based on the pressure detected by each of the pressure sensors, compares the cylinder gas residual quantity in each of the gas cylinders with a gas consumption quantity assumed to be used for each gas type by the gas analysis device and manages a timing to replace each of the gas cylinders.

In accordance with this arrangement, since the timing to replace each of the gas cylinders is managed by calculating the cylinder gas residual quantity of the multiple gas cylinders by the use of the multiple pressure sensors that detect the pressure of each of the multiple gas cylinders, it becomes possible to collectively manage the timing to replace the multiple gas cylinders. In addition, since the timing to replace each of the gas cylinders is managed, there is no need of going to a cylinder chamber and verifying the cylinder gas residual quantity so that it is possible to shorten a period to interrupt an experiment and a test. In addition, it becomes possible to reduce human errors due to confirmation mistakes.

A test system such as an exhaust gas analysis system comprises multiple gas analysis devices. In order to preferably use this test system, it is preferable that the management device accumulates the gas consumption quantity assumed to be used for each gas type by the multiple gas analysis devices, and compares the accumulated gas consumption quantity with the cylinder gas residual quantity in each of the gas cylinders.

It is preferable that the management device manages the timing to replace the cylinder by comparing the cylinder gas residual quantity of each gas cylinder with the gas consumption quantity assumed to be used for each gas type by the multiple gas analysis devices.

In accordance with this arrangement, since the timing to replace the gas cylinder can be managed in consideration with the assumed gas consumption quantity, it is possible to replace the gas cylinder before the residual quantity of the cylinder gas reaches zero. As a result of this, it is possible to shorten the stand-by time while the test is interrupted.

It is preferable that the management device obtains a test schedule for each of the multiple gas analysis devices and calculates the gas consumption quantity assumed to be used by the multiple gas analysis devices for each gas type based on these test schedules.

In accordance with this arrangement, since the gas consumption quantity (assumed) to be used by each of the gas analysis devices can be previously anticipated, it is possible to replace the gas cylinder before the cylinder gas residual quantity reaches zero. As this result, it becomes possible not to interrupt the test.

Some gas type in the gas cylinder is used apart from the test schedule. In order to manage the timing to replace the gas cylinder more accurately, it is preferable that the management device uses a total value of the gas consumption quantity based on the test schedule and the gas consumption quantity used aside from the test schedule as the gas consumption quantity assumed to be used by the multiple gas analysis devices for each gas type.

It is preferable that the management device uses the gas consumption quantity in maintenance of a predetermined cycle set for each of the multiple gas analysis devices as the gas consumption quantity used aside from the test schedule.

It is preferable that the management device manages the timing to replace the gas cylinder based on a delivery date of the gas cylinder.

In accordance with this arrangement, it is possible to replace the gas cylinder without making the cylinder gas residual quantity of the gas cylinder zero.

In order to manage the timing to replace the gas cylinder more accurately, it is preferable that the management device has a machine learning part that anticipates the timing to replace the gas cylinder based on a machine learning algorithm by the use of a gas type, a gas residual pressure of the gas cylinder and the test schedule as input parameters.

In addition, a cylinder management method in accordance with this invention is a cylinder management method that manages multiple gas cylinders that supply a cylinder gas to a gas analysis device that analyzes an exhaust gas of a specimen as being a vehicle or a part of the vehicle, and that comprises steps of detecting a pressure of each of the multiple gas cylinders by providing a pressure sensor to each of the multiple gas cylinders, and calculating a cylinder gas residual quantity in each of the gas cylinders based on the pressure detected by each of the pressure sensors, and comparing the cylinder gas residual quantity in each of the gas cylinders with a gas consumption quantity assumed to be used for each gas type by the gas analysis device so that a timing to replace each of the gas cylinders is managed.

Furthermore, a cylinder management program in accordance with this invention is a cylinder management program that is used for a system having multiple gas cylinders that supply a cylinder gas to a gas analysis device that analyzes an exhaust gas of a specimen as being a vehicle or a part of the vehicle and multiple pressure sensors each of which detects a pressure of each of the multiple gas cylinders, and is characterized by providing a computer with functions as a cylinder gas residual quantity calculating part that calculates a cylinder gas residual quantity in each of the gas cylinders based on the detected pressure of each of the pressure sensors, and a replace timing managing part that compares the cylinder gas residual quantity in each of the gas cylinders with a gas consumption quantity assumed to be used for each gas type by the gas analysis device and manages a timing to replace each of the gas cylinders.

In addition, a gas leak detection system in accordance with this invention is a gas leak detection system that detects a gas leak between a gas analysis device that analyzes an exhaust gas of a specimen as being a vehicle or a part of the vehicle and multiple gas cylinders that supply a cylinder gas to the gas analysis device, and is characterized by comprising multiple pressure sensors each of which detects a pressure of each of the multiple gas cylinders, a flow rate sensor that detects a flow rate of a fluid flowing in the gas analysis device, and a management device that calculates a cylinder gas residual quantity in each of the gas cylinders based on the pressure detected by each of the pressure sensors, calculates a gas consumption quantity of the gas analysis device based on the detected flow rate of the flow rate sensor, and detects the gas leak based on the cylinder gas residual quantity and the gas consumption quantity.

In accordance with this arrangement, since the cylinder gas residual quantity of each gas cylinder is calculated based on the pressure detected by each pressure sensor, the gas consumption quantity of the gas analysis device is calculated from the flow rate detected by the flow rate sensor and the gas leak is detected based on the cylinder gas residual quantity and the gas consumption quantity, it is possible to collectively monitor the gas leak in the system wherein the multiple gas cylinders are connected to the gas analysis device.

Effect of the Invention

In accordance with this invention having this arrangement, it is possible to collectively manage the timing to replace the multiple cylinders.

MODE FOR EMBODYING THE INVENTION

One embodiment of a cylinder management system in accordance with this invention will be explained with reference to drawings.

Figure 1:
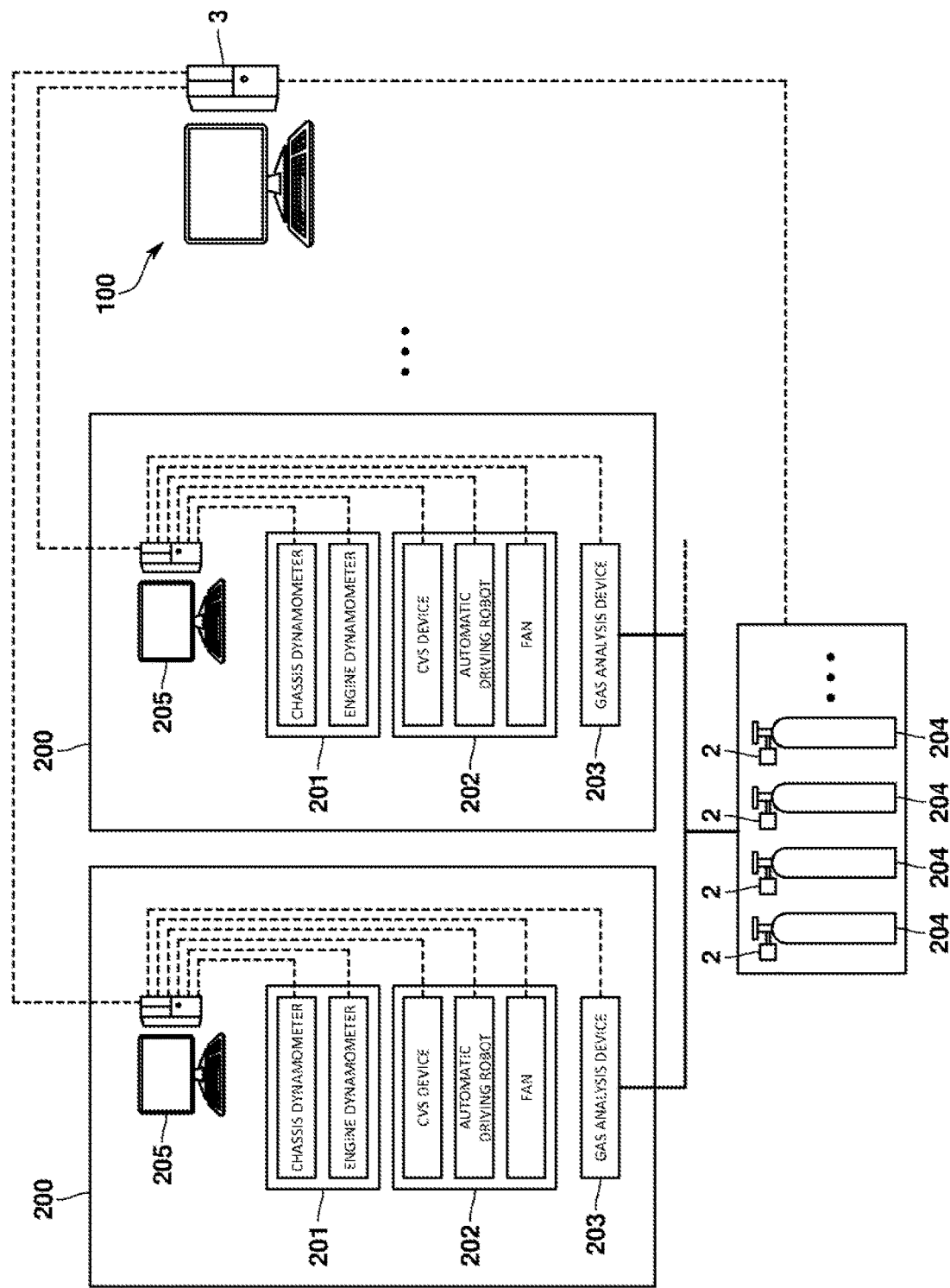
FIG. 1 is a schematic diagram showing a configuration of an exhaust gas analysis system of this embodiment.

The cylinder management system 100 of this embodiment, as shown in FIG. 1, is used for managing a gas cylinder 204 of one or multiple exhaust gas analysis systems 200 that analyze an engine exhaust gas discharged from a specimen as being a vehicle or a part of the vehicle. The specimen is a vehicle, an engine or a power train (a vehicle driving system).

One or multiple exhaust gas analysis systems 200 are used for a test on the specimen, and comprise a load device 201 such as a chassis dynamometer on which a vehicle is loaded, an engine dynamometer connected to an output shaft of an engine or a driving system test facility to test a vehicle driving system, a test facility 202 such as a CVS device that samples an exhaust gas discharged from the specimen, an automatic driving robot or a fan, one or multiple gas analysis devices 203 that analyze a component to be measured in the exhaust gas, multiple gas cylinders 204 that supply a cylinder gas (a utility gas or a calibration gas in this embodiment) to one or the multiple gas analysis devices 203 and a control unit 205 that controls the load device 201, the test facility 202 or the gas analysis device 203 and that conducts the exhaust gas test based on a predetermined test schedule. One or the multiple exhaust gas analysis systems 200 may be arranged in a building or separately arranged in multiple buildings. The predetermined test schedule contains, for example, an exhaust gas certification test that corresponds to an enactment in each country, and may contain a cold start test, a transient test, a hot start test, a running gloss transpiration gas test, a hot soak transpiration gas test and a diurnal transpiration gas test. The test schedule is set by a user in advance.

The utility gas is a gas that is necessary at a time of analyzing the exhaust gas by the gas analysis device 203, and for example, $H_2$ gas or $O_2$ gas. In addition, the calibration gas is a gas that is necessary at a time of calibrating the gas analysis device 203, the calibration gas for span calibration is, for example, CO gas, $CO_2$ gas, $C_3H_8$ gas, $CH_4$ gas, NO gas, $NO_2$ gas and $N_2O$ gas, and the calibration gas for zero calibration is, for example, $N_2$ gas. The calibration gas for span calibration is prepared for each concentration. A kind of the used gas or the concentration of the used gas is determined according to the test schedule by the gas analysis device (for low concentration, for high concentration). The gas analysis device is selected according to the gas for a passenger car, for a truck, for a gasoline-powered vehicle, for a diesel vehicle or for a natural gas vehicle.

The multiple gas cylinders 204 may be collectedly arranged in a single cylinder chamber, or separately arranged in multiple cylinder chambers or in a predetermined portion. The multiple gas analysis devices 203 to which the gas is supplied from each gas cylinder 204 may be contained in a single exhaust gas analysis system 200 or may be contained in the multiple exhaust gas analysis systems 200.

The cylinder management system 100 manages the multiple gas cylinders 204 by the use of the pressure of each of the multiple gas cylinders 204.

Figure 2:
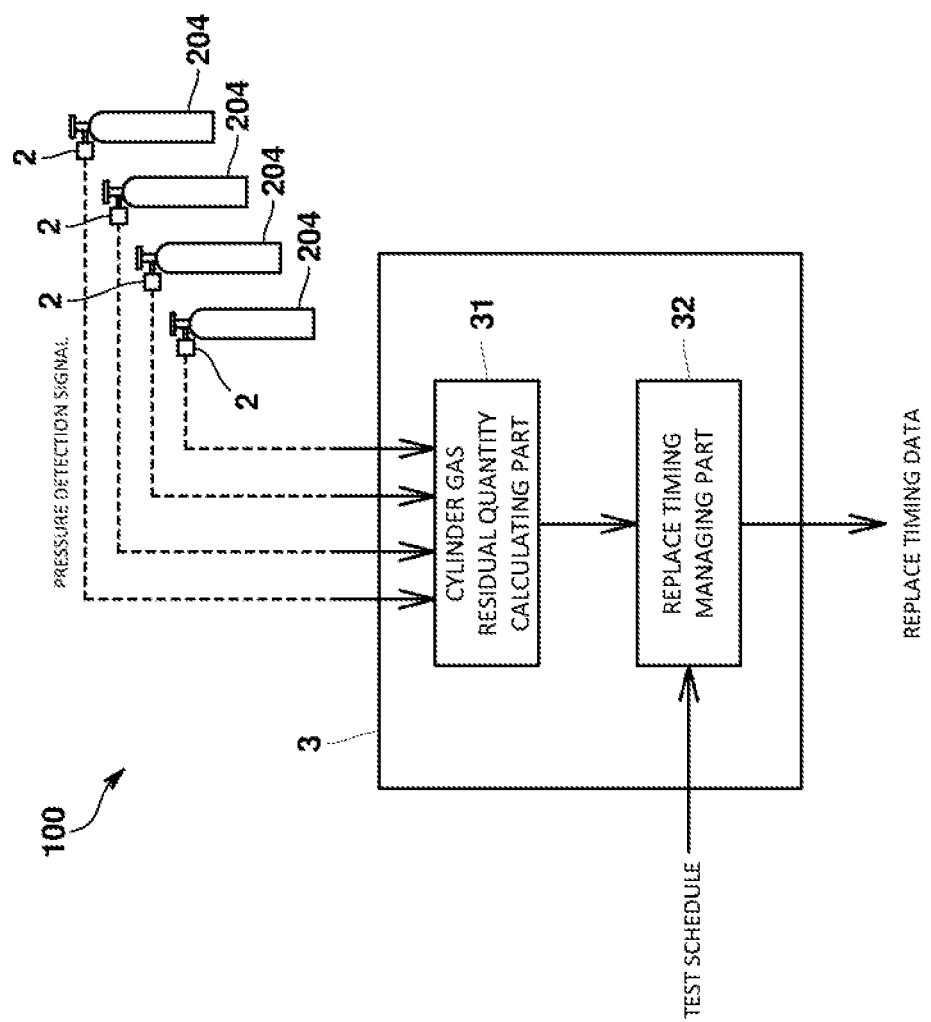
FIG. 2 is a schematic diagram showing a configuration of a cylinder management system of this embodiment.

Concretely, the cylinder management system 100 comprises, as shown in FIG. 2, multiple pressure sensors 2 that detect the pressure of each of the multiple gas cylinders 204 and a management device 3 that calculates a cylinder gas residual quantity in each gas cylinder 204 based on the pressure detected by each of the pressure sensors 2, and manages a timing to replace each gas cylinder 204.

The pressure sensor 2 is arranged for each gas cylinder 204. The pressure sensor 2 may be fixed to the gas cylinder 204, or may be post installed to an output port of the gas cylinder 204. The pressure detection signal of the pressure sensor 2 is output to the management device 3 through a wired or wireless communication circuit.

The management device 3 is a dedicated or general purpose device having a CPU, an internal memory, an input/output interface, an input device such as a key board or a mouse, an output device such as a display or a printer and a communication device that is communicable to the pressure sensor 2 or the control unit 205 through the communication circuit.

The management device 3 produces functions as a cylinder gas residual quantity calculating part 31 and a replace timing managing part 32 by cooperatively working with the CPU and its peripheral devices based on cylinder management programs stored in the internal memory.

The cylinder gas residual quantity calculating part 31 receives the pressure detection signal of the multiple pressure sensors 2 on a constant basis or intermittently, and calculates the cylinder gas residual quantity of each gas cylinder 204. Concretely, the cylinder gas residual quantity calculating part 31 calculates the cylinder gas residual quantity (unit: L) based on an electric current signal (unit: mA) output from each of the pressure sensors 2.

The replace timing managing part 32 compares the cylinder gas residual quantity (R) of each gas cylinder 204 with the gas consumption quantity (U) assumed to be an accumulated quantity for each gas kind in the multiple gas analysis device 203, and estimates and manages the timing to replace each gas cylinder 204. The timing to replace the gas cylinder 204 may be a date, and may be a period from the present (for example, 30 days later).

In addition, the replace timing managing part 32 obtains each test schedule of the multiple gas analysis devices 203 from the control unit 205 and calculates the gas consumption quantity (U) assumed to be used by all of the multiple gas analysis devices 203 for each gas type.

The gas consumption quantity (U) assumed to be used for each gas type is a total value $(U_1+U_2)$ of a gas consumption quantity $U_1$ based on the test schedule and a gas consumption quantity $U_2$ used aside from the test schedule. The gas consumption quantity $U_2$ used aside from the test schedule is, for example, a gas consumption quantity during a maintenance conducted at a predetermined cycle (for example, once a month) set for each of the multiple gas analysis devices 203.

Figure 3:
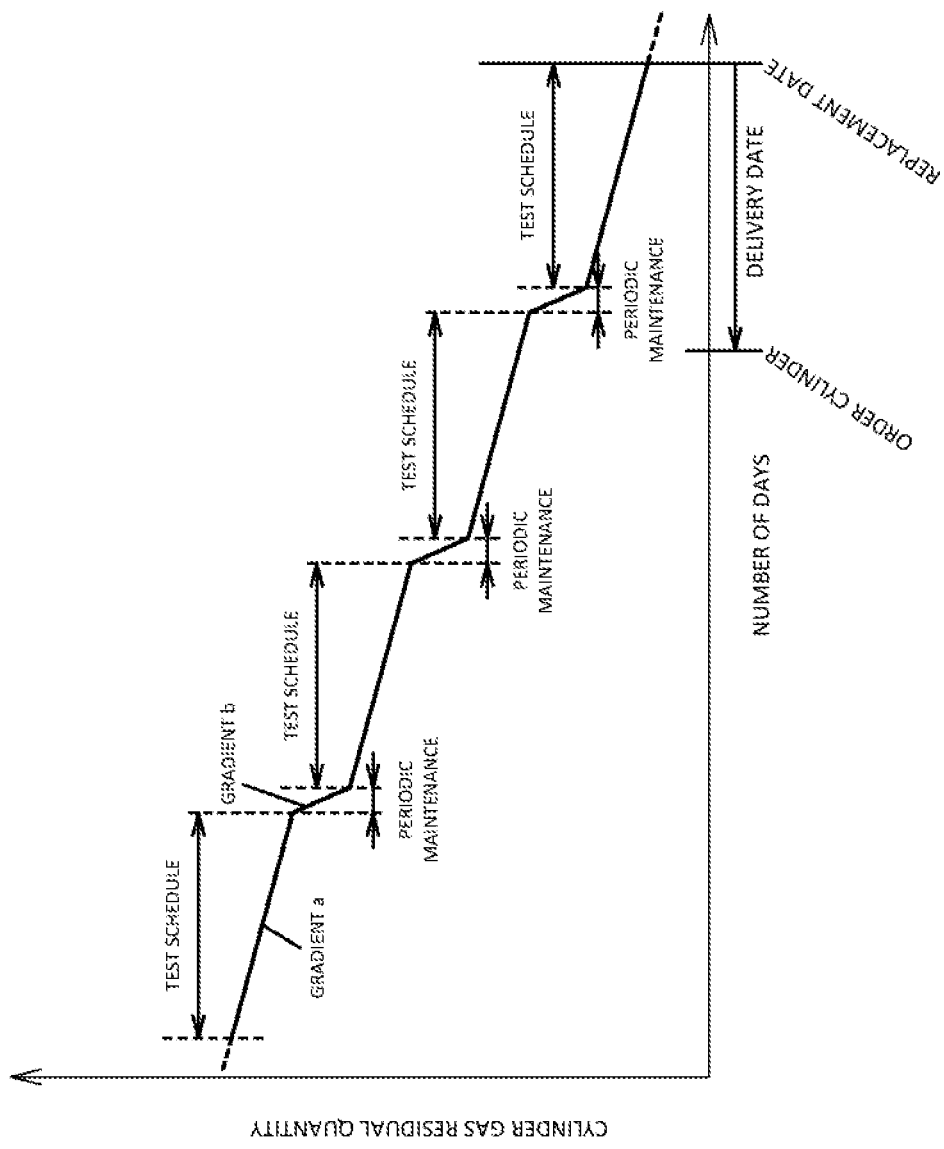
FIG. 3 is a schematic diagram showing a chronological change of a cylinder gas residual quantity in a gas cylinder

Concretely, as shown in FIG. 3, the replace timing managing part 32 calculates the timing to replace the gas cylinder 204 by the use of the following expression.

$$0 \leq \text{(cylinder gas residual quantity}(R)) - \text{(number of days until replacement)} \times a - \text{(number of days until replacement)} \times b$$

The coefficient "a" is an average gradient of the gas consumption quantity $U_1$ consumed in the test schedule. The coefficient "a" may be a value that differs in accordance with the gas analysis device 203 to be used. In addition, the coefficient "a" may be changed in accordance with a content of the test schedule.

In addition, the coefficient "b" is an average gradient of the gas consumption quantity $U_2$ consumed during calibration that is conducted periodically. The coefficient "b" may be a value that differs in accordance with the gas analysis device 203 to be used.

Furthermore, the replace timing managing part 32 also manages the timing to replace the gas cylinder 204 based on the delivery date of the gas cylinder 204. In this case, the replace timing managing part 32 calculates the timing to replace the gas cylinder 204 by the use of the following expression.

$$0 \leq \text{(cylinder gas residual quantity}(R)) - \text{(number of days until replacement+delivery date)} \times a - \text{(number of days until replacement+delivery date)} \times b$$

The number of days until replacement (timing to replace) calculated by the above-mentioned expression is displayed on a display of the management device 3. In addition, in case that the timing to replace the gas cylinder 204 is shorter than a predetermined cycle, a reporting means to issue an alarm to urge the user to replace the gas cylinder 204 may be provided. Furthermore, the management device 3 may have an ordering part that automatically places an order of the gas cylinder based on the calculated timing to replace the gas cylinder 204.

Effect of this Embodiment

In accordance with the cylinder management system 100 of this embodiment, since the cylinder gas residual quantity (R) of the multiple gas cylinders 204 is calculated by the use of the multiple pressure sensors 2 each of which detects the pressure of each of the multiple gas cylinders 204, and the timing to replace each gas cylinder 204 is anticipated and managed, it becomes possible to collectively manage the timing to replace the multiple gas cylinders 204. In addition, since the timing to replace each gas cylinder 204 is anticipated and managed, there is no need of going to the cylinder chamber and verifying the cylinder gas residual quantity (R) so that it is possible to shorten a period to interrupt the experiment and the test. In addition, it becomes possible to reduce human errors due to confirmation mistakes.

Other Embodiment

This invention is not limited to the above-mentioned embodiment.

Figure 4:
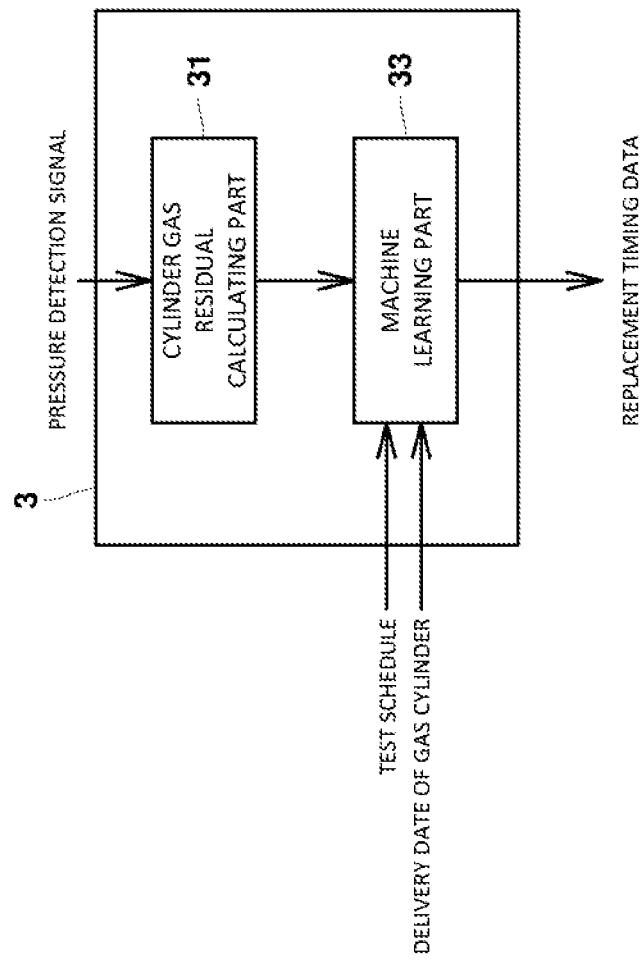
FIG. 4 is a schematic diagram showing a configuration of a cylinder management system of a modified embodiment.

For example, as shown in FIG. 4, the management device 3 may have a machine learning part 33 that anticipates the timing to replace the gas cylinder 204 by the use of machine learning algorithm. Concretely, the machine learning part 33 anticipates the timing to replace each gas cylinder 204 based on the machine learning algorithm by the use of the gas type, a cylinder gas residual pressure of each gas cylinder 204, the test schedule of each gas analysis device 203 and the delivery date of each gas cylinder 204 as the input parameters. In addition, the machine learning part 33 may update the coefficient "a" and the coefficient "b" of the above-mentioned embodiment by the use of the machine learning algorithm.

The replace timing managing part 32 may manage the timing to replace the gas cylinder 204 by comparing the cylinder gas residual quantity obtained by the cylinder gas residual quantity calculating part 31 with the gas consumption quantity in the test schedule of each gas analysis device 203 without using the calculation formula of the above-mentioned embodiment. In this case, the replace timing managing part 32 roughly estimates the gas consumption quantity in the test schedule of each gas analysis device 203, and manages the timing to replace the gas cylinder 204 by comparing the roughly estimated gas consumption quantity with the cylinder gas residual quantity.

In addition, the management device 3 in the above-mentioned embodiment may have a function of detecting a gas leak between the multiple gas analysis devices 203 and the multiple gas cylinders 204. In this case, as shown in FIG. 5, the exhaust gas analysis system 200 is provided with multiple flow rate sensors 4 that detect a flow rate of a fluid that flows in each of the multiple gas analysis devices 203.

Figure 5:
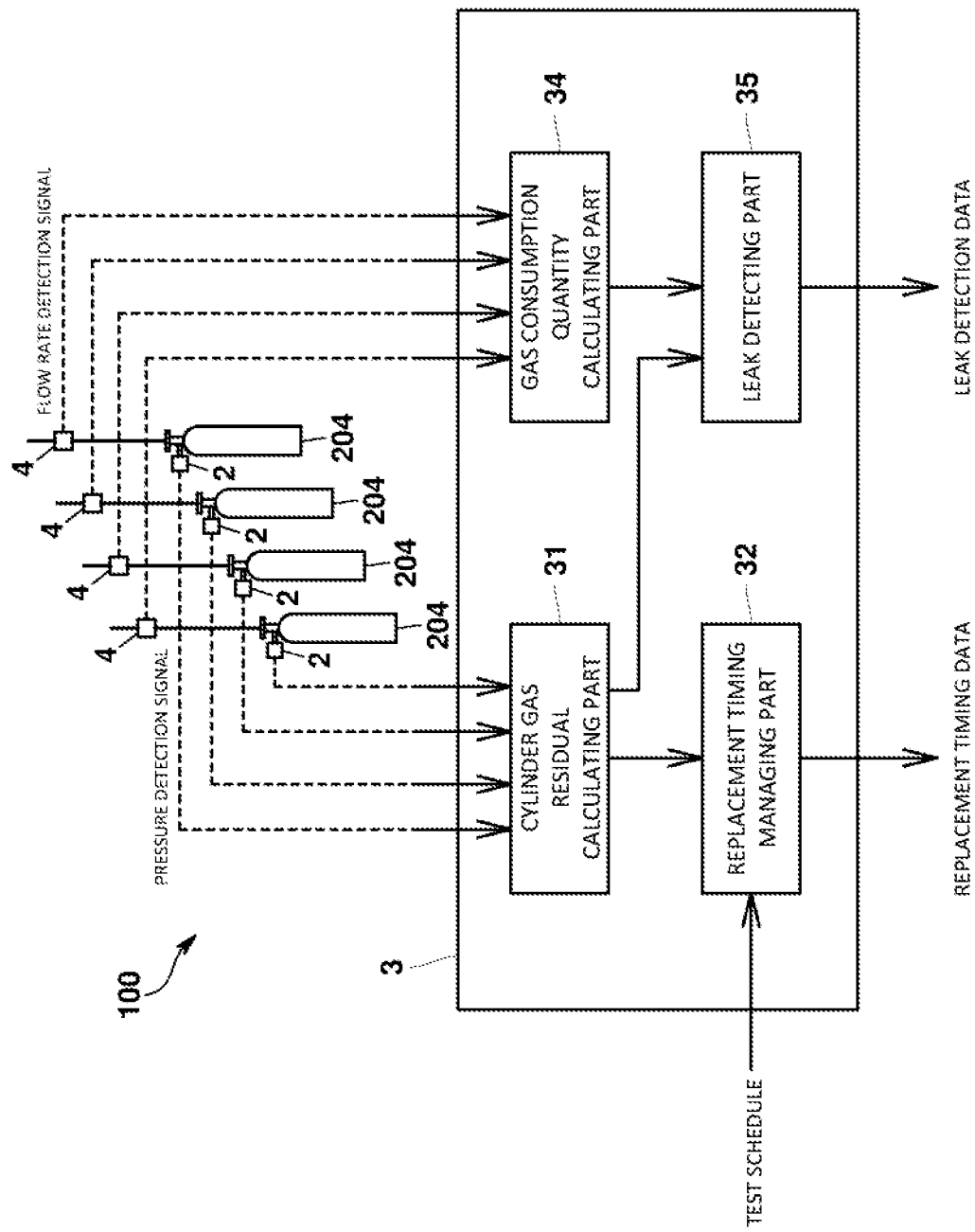
FIG. 5 is a schematic diagram showing a configuration of a cylinder management system of a modified embodiment.

As shown in FIG. 5, in addition to the cylinder gas residual quantity calculating part 31, the management device 3 has a gas consumption quantity calculating part 34 that calculates the gas consumption quantity of each gas analysis device 203 from the detected flow rate of each flow rate sensor 4, and a leak detecting part 35 that detects the gas leak from the cylinder gas residual quantity and the gas consumption quantity. The leak detecting part 35 compares the gas consumption quantity obtained from the cylinder gas residual quantity with the gas consumption quantity obtained from the detected flow rate of the flow rate sensor 4. In case that the difference is out of a predetermined range, the leak detecting part 35 judges that the gas leak occurs. It is preferable to provide a reporting means to issues an alarm that reports the occurrence of the gas leak.

The management device 3 may have only the function of detecting the gas leak without managing the timing to replace the gas cylinder.

Various modifications or combinations of the embodiments may be made without departing from the spirit of this invention.

DESCRIPTION OF THE REFERENCE NUMERALS

100 . . . cylinder management system
203 . . . gas analysis system
204 . . . gas cylinder
2 . . . pressure sensor
R . . . cylinder gas residual quantity
U . . . gas consumption quantity
$U_1$ . . . gas consumption quantity based on test schedule
$U_2$ . . . gas consumption quantity used during maintenance
3 . . . management device
31 . . . cylinder gas residual quantity calculating part
32 . . . replace timing managing part
33 . . . machine learning part
34 . . . gas consumption quantity calculating part
35 . . . leak detecting part

The invention claimed is:

1. A cylinder management system that manages multiple gas cylinders that supply a cylinder gas to multiple gas analysis devices that analyze an exhaust gas of a vehicle or a part of the vehicle, comprising:
    multiple pressure sensors each of which detects a pressure of each of the gas cylinders, and
    a management device that
        calculates a cylinder gas residual quantity in each of the gas cylinders based on the pressure detected by each of the pressure sensors,
        compares the cylinder gas residual quantity in each of the gas cylinders with an expected gas consumption quantity, which is a quantity of gas expected to be used for each gas type by the gas analysis devices,
        calculates a total gas consumption quantity by adding up the expected gas consumption quantity for each gas type by the gas analysis devices,
        compares the total gas consumption quantity with the cylinder gas residual quantity in each of the gas cylinders,
        obtains a test schedule for each of the gas analysis devices,
        calculates the expected gas consumption quantity of the gas analysis devices for each gas type based on the test schedules, and
        manages a timing to replace each of the gas cylinders.

2. The cylinder management system described in claim 1, wherein
    the management device uses a total value of the gas consumption quantity based on the test schedule and the gas consumption quantity used aside from the test schedule as the expected gas consumption quantity to be used by the gas analysis devices for each gas type.

3. The cylinder management system described in claim 2, wherein
    the management device uses the gas consumption quantity in maintenance of a predetermined cycle set for each of the gas analysis devices as the gas consumption quantity used aside from the test schedule.

4. The cylinder management system described in claim 1, wherein
    the management device manages the timing to replace the gas cylinder based on a delivery date of the gas cylinder.

5. The cylinder management system described in claim 1, wherein
    the management device has a machine learning part that anticipates the timing to replace the gas cylinder based on a machine learning algorithm by the use of a gas type, a gas residual pressure of the gas cylinder, and the test schedule as input parameters.

6. A cylinder management method that manages multiple gas cylinders that supply a cylinder gas to multiple gas analysis devices that analyze an exhaust gas of a vehicle or a part of the vehicle, the method comprising:
    detecting a pressure of each of the gas cylinders by providing a pressure sensor to each of the gas cylinders;
    calculating a cylinder gas residual quantity in each of the gas cylinders based on the pressure detected by each of the pressure sensors;
    comparing the cylinder gas residual quantity in each of the gas cylinders with an expected gas consumption quantity which is a quantity of gas expected to be used for each gas type by the gas analysis devices;

calculating a total gas consumption quantity by adding up the expected gas consumption quantity for each gas type by the gas analysis devices;

comparing the total gas consumption quantity with the cylinder gas residual quantity in each of the gas cylinders;

obtaining a test schedule for each of the gas analysis devices; and calculating the expected gas consumption quantity of the gas analysis devices for each gas type based on the test schedules so that a timing to replace each of the gas cylinders is managed.

7. A cylinder management non-transitory program that is used for a system having multiple gas cylinders that supply a cylinder gas to multiple gas analysis devices that analyze an exhaust gas of a vehicle or a part of the vehicle and multiple pressure sensors each of which detects a pressure of each of the gas cylinders, providing a computer with functions as calculating a cylinder gas residual quantity in each of the gas cylinders based on the detected pressure of each of the pressure sensors, comparing the cylinder gas residual quantity in each of the gas cylinders with an expected gas consumption quantity which is a quantity of gas expected to be used for each gas type by the gas analysis devices, calculating a total gas consumption quantity by adding up the expected gas consumption quantity for each gas type by the gas analysis devices, comparing the total gas consumption quantity with the cylinder gas residual quantity in each of the gas cylinders, obtaining a test schedule for each of the gas analysis devices, calculating the expected gas consumption quantity of the gas analysis devices for each gas type based on the test schedules, and managing a timing to replace each of the gas cylinders.

\* \* \* \* \*